(12) United States Patent
Urasaki et al.

(10) Patent No.: US 12,035,878 B2
(45) Date of Patent: Jul. 16, 2024

(54) ENDOSCOPE SYSTEM FOR ASSIGING MULTIPLE FUNCTIONS TO A SWITCH, CONTROL METHOD OF ENDOSCOPE SYSTEM AND STORAGE MEDIUM

(71) Applicant: OLYMPUS CORPORATION, Tokyo (JP)

(72) Inventors: Takeshi Urasaki, Tachikawa (JP); Koichi Niida, Hachioji (JP); Masaki Kondo, Hachioji (JP); Takuya Ogura, Hachioji (JP); Aki Matsumoto, Sagamihara (JP); Ryunosuke Matsushige, Hachioji (JP); Satoru Ono, Akishima (JP); Takahiro Yumoto, Tokyo (JP); Hideyuki Wada, Hino (JP); Sachiko Hashimoto, Hachioji (JP); Tomomi Ouchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 847 days.

(21) Appl. No.: 17/105,812

(22) Filed: Nov. 27, 2020

(65) Prior Publication Data

US 2021/0076903 A1 Mar. 18, 2021

Related U.S. Application Data

(63) Continuation of application No. PCT/JP2019/020131, filed on May 21, 2019.

(30) Foreign Application Priority Data

May 28, 2018 (JP) ................................. 2018-101600

(51) Int. Cl.
*A61B 1/00* (2006.01)
*H04N 5/92* (2006.01)

(52) U.S. Cl.
CPC ........ *A61B 1/00006* (2013.01); *A61B 1/0002* (2013.01); *A61B 1/0004* (2022.02);
(Continued)

(58) Field of Classification Search
None
See application file for complete search history.

(56) References Cited

U.S. PATENT DOCUMENTS 6,120,435 A * 9/2000 Eino .................. A61B 1/00042
348/E5.042
8,686,890 B2 * 4/2014 Moorer ............ H04N 21/42206
341/173

(Continued)

FOREIGN PATENT DOCUMENTS

EP 1 779 767 A1 5/2007
EP 2336848 B1 7/2017
(Continued)

OTHER PUBLICATIONS

International Search Report dated Aug. 13, 2019 received in PCT/JP2019/020131.

*Primary Examiner* — John P Leubecker
(74) *Attorney, Agent, or Firm* — Scully, Scott, Murphy & Presser, P.C.

(57) ABSTRACT

An endoscope system includes an endoscope including at least one switch, each of which can be assigned two functions, and a controller. The controller sets a plurality of function pairs, each of which is composed of a combination of any one of a plurality of first functions and any one of a plurality of second functions, and assigns one function pair selected from the plurality of function pairs to the switch, measures a switch pressing time period after the switch is pressed, and executes the first function when the switch pressing is released before a predetermined first time period (Continued)

elapses after the switch is pressed and executes the second function when the switch pressing time period passes the first time period.

17 Claims, 10 Drawing Sheets

(52) U.S. Cl.
CPC ........ *A61B 1/00043* (2013.01); *A61B 1/0005* (2013.01); *H04N 5/9201* (2013.01)

(56) References Cited

U.S. PATENT DOCUMENTS

| | | | |
|---|---|---|---|
| 2002/0030661 A1* | 3/2002 | Gemunder | G06F 3/023 345/156 |
| 2006/0062382 A1* | 3/2006 | Ronkainen | G06F 3/04895 345/184 |
| 2006/0173240 A1* | 8/2006 | Fukuyama | A61B 1/043 600/118 |
| 2007/0123749 A1* | 5/2007 | Iwasaki | A61B 1/00055 600/117 |
| 2010/0104264 A1* | 4/2010 | Rumreich | H04N 21/8106 348/E3.047 |
| 2011/0128233 A1* | 6/2011 | Aoike | G06F 3/04895 345/170 |
| 2011/0242301 A1* | 10/2011 | Morita | A61B 1/000094 382/128 |
| 2013/0021252 A1* | 1/2013 | Lu | G06F 3/048 345/173 |
| 2013/0300829 A1* | 11/2013 | Urasaki | A61B 1/00194 348/45 |
| 2018/0184881 A1* | 7/2018 | Urasaki | A61B 1/00006 |

FOREIGN PATENT DOCUMENTS

| | | | |
|---|---|---|---|
| JP | 10-276973 A | | 10/1998 |
| JP | 2004-033333 A | | 2/2004 |
| JP | 2006-034815 A | | 2/2006 |
| JP | 2006-167139 A | | 6/2006 |
| JP | 2010-045568 A | | 2/2010 |
| JP | 2012040168 A | * | 3/2012 |
| JP | 2014-035163 A | | 2/2014 |
| JP | 2017-070477 A | | 4/2017 |
| WO | 2006/011509 A1 | | 2/2006 |
| WO | 2010/018740 A1 | | 2/2010 |

* cited by examiner

ENDOSCOPE SYSTEM FOR ASSIGING MULTIPLE FUNCTIONS TO A SWITCH, CONTROL METHOD OF ENDOSCOPE SYSTEM AND STORAGE MEDIUM

CROSS REFERENCE TO RELATED APPLICATION

This application is a continuation application of PCT/JP2019/020131 filed on May 21, 2019 and claims benefit of Japanese Application No. 2018-101600 filed in Japan on May 28, 2018, the entire contents of which are incorporated herein by this reference.

BACKGROUND OF THE INVENTION

1. Field of the Invention

The present invention relates to an endoscope system, a control method of the endoscope system and a storage medium.

2. Description of the Related Art

Conventionally, endoscope systems have been widely used in a medical field and the like. Observation images of objects picked up by endoscopes are used for a variety of uses such as recording of diagnoses and cases, and explanations to patients or the like. The observation images are normally displayed on a screen or saved in a recording apparatus with information such as patient information and observation parameters added to identify individual observation images. However, depending on the use, for example explanations to patients, such information may have to be selectively excluded and only observation images have to be displayed or saved.

An operation portion of a common endoscope is provided with one or a plurality of operation switches and several operation functions, which are frequently used, among operations that can be performed on an operation panel of a processor for the endoscope are assigned to the switches. By operating these switches, operators can remotely operate the processor for the endoscope, and can thereby perform operations without touching a non-washable operation panel.

In a conventional endoscope system, since one function is assigned to one operation switch, for example, when a function to acquire an observation image with patient information or the like added and a function to acquire only an observation image with no information added are preferably used separately, at least two operation switches are necessary.

As functions of endoscope systems become more and more diversified, the number of operation functions that have to be frequently used during surgery in addition to the above functions, is on the increase and there is a growing need to increase the number of operation switches. However, due to space limitations of the operation portion, it is difficult to install as many operation switches as the number of necessary functions. Therefore, for example, Japanese Patent Application Laid-Open Publication No. 2006-167139 proposes an endoscope system that gives one operation switch a plurality of functions such that the plurality of functions are switched according to the amount of pressing of the switch.

SUMMARY OF THE INVENTION

An endoscope system according to one aspect of the present invention includes an endoscope including at least one switch, each of which can be assigned two functions, and a controller. The controller is configured to set a plurality of function pairs, each of which is composed of a combination of any one of a plurality of first functions and any one of a plurality of second functions, and assign one function pair selected from the plurality of function pairs to the switch, measure a switch pressing time period after the switch is pressed, and execute the first function when the switch pressing is released before a predetermined first time period elapses after the switch is pressed and executes the second function when the switch pressing time period passes the first time period.

A control method of an endoscope system according to one aspect of the present invention includes setting a plurality of function pairs, each of which is composed of a combination of any one of a plurality of first functions and any one of a plurality of second functions, and assigning one function pair selected from the plurality of function pairs to a switch, measuring a switch pressing time period after the switch is pressed, and executing the first function when the switch pressing is released before a predetermined first time period elapses after the switch is pressed and executing the second function when the switch pressing time period passes the first time period.

A storage medium according to one aspect of the present invention is a non-transitory computer-readable storage medium that stores a control program of an endoscope system. The control program causes a computer to: set a plurality of function pairs, each of which is composed of a combination of any one of a plurality of first functions and any one of a plurality of second functions, and assign one function pair selected from the plurality of function pairs to a switch; measure a switch pressing time period after the switch is pressed, and execute the first function when the switch pressing is released before a predetermined first time period elapses after the switch is pressed and executing the second function when the switch pressing time period passes the first time period.

DETAILED DESCRIPTION OF THE PREFERRED EMBODIMENTS

Hereinafter, embodiments will be described with reference to the drawings.

First Embodiment

Figure 1:
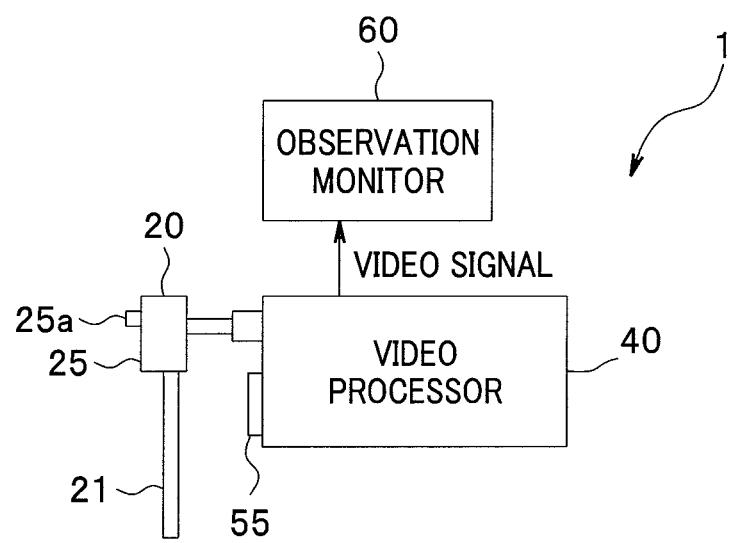
FIG. 1 is a schematic diagram illustrating an example of an overall configuration of an endoscope system according to an embodiment of the present invention.

FIG. 1 is a schematic diagram illustrating an example of an overall configuration of an endoscope system according to an embodiment of the present invention. As illustrated, for example, in FIG. 1, an endoscope system 1 is constructed of an endoscope 20 configured to be inserted into a body cavity to observe or treat an affected region and a video processor 40 configured to apply predetermined signal processing to a video signal captured by the endoscope 20. A monitor 60 configured to display a video subjected to signal processing is connected to the video processor 40. As the monitor 60, a normal color monitor may be used.

Figure 2:
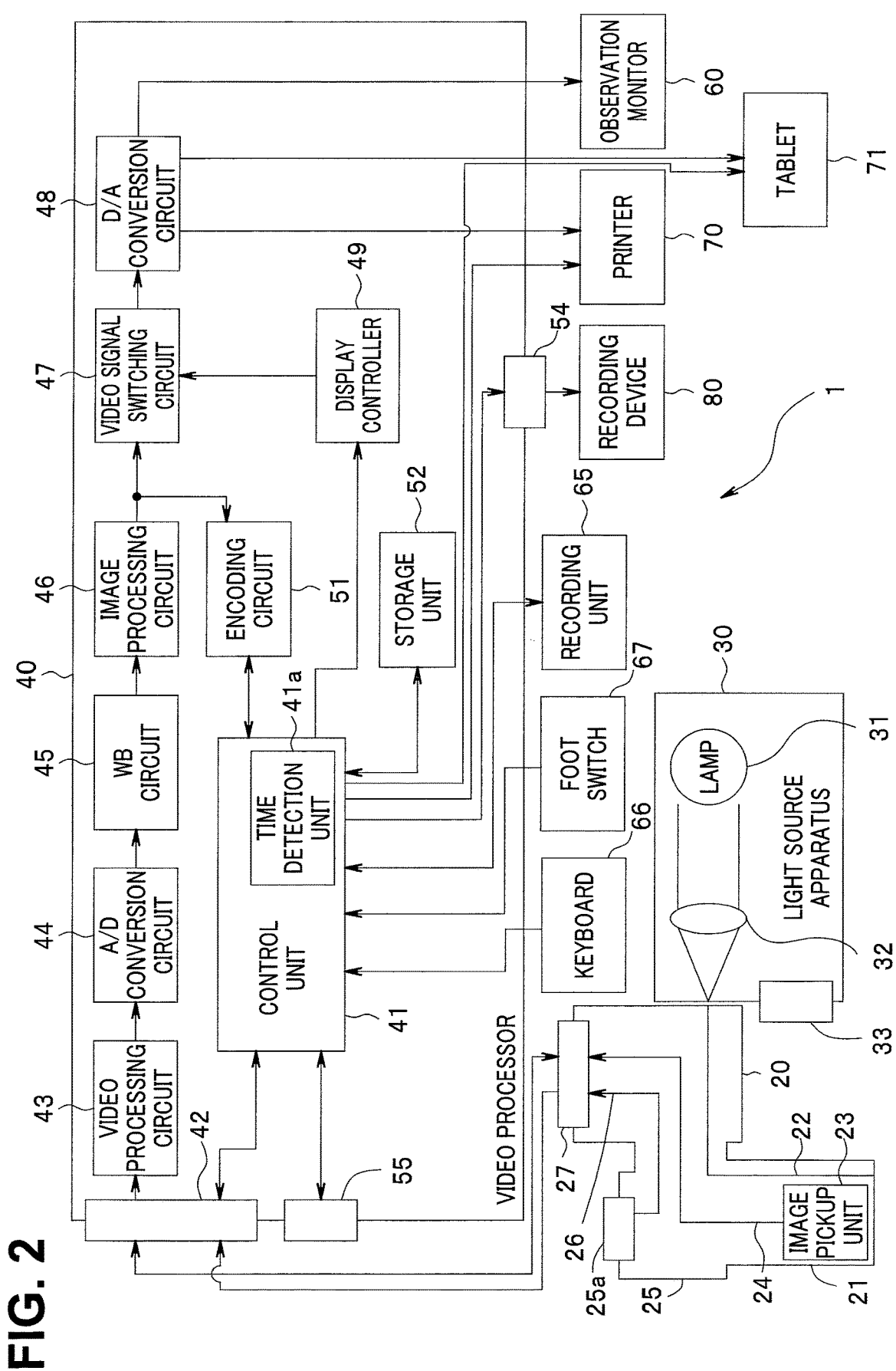
FIG. 2 is a block diagram illustrating a detailed configuration of the endoscope system according to the embodiment of the present invention.

FIG. 2 is a schematic block diagram illustrating a detailed configuration of the endoscope system. As illustrated in FIG. 2, the endoscope 20 is provided with an elongated insertion portion 21 to be inserted into a body cavity. An operation portion 25 is provided at a rear end of the insertion portion 21 and the operation portion 25 is provided with a connector 27. The endoscope 20 is electrically connected to the video processor 40 via the connector 27 and a connector 42 provided for the video processor 40. Note that FIG. 2 illustrates an example of signal transmission between the endoscope 20 and the video processor 40 by wired transmission, but signal transmission may be performed by wireless transmission.

A light guide 22 configured to transmit illumination light from a light source apparatus 30 is inserted in the insertion portion 21 and the operation portion 25 of the endoscope 20. The light source apparatus 30 includes a lamp 31 and a condensing lens 32 so as to guide illumination light from the lamp 31 to an incident end of the light guide 22 via the lens 32. The light source apparatus 30 is provided with an operation panel 33. The user can set the light source apparatus 30 by operating the operation panel 33. Note that FIG. 2 illustrates an example where the video processor 40 and the light source apparatus 30 are made up of separate units, but the video processor and the light source apparatus may be integrally constructed.

As the light source apparatus 30, a semiconductor light-emitting device such as an LED or a laser diode may be used instead of the lamp 31. When the semiconductor light-emitting device is used, a type of semiconductor light-emitting device that emits white light may be used or a type of semiconductor light-emitting device that multiplexes light beams emitted from a plurality of semiconductor light-emitting devices having different RGB color components to obtain white light may be used. A light source apparatus may be provided at a distal end of the insertion portion 21 of the endoscope 20.

The endoscope 20 transmits illumination light from the light source apparatus 30 through the light guide 22 and emits the illumination light from the distal end portion of the insertion portion 21 to an object. An image pickup unit 23 is provided at the distal end portion of the insertion portion 21. The image pickup unit 23 includes an optical system not shown configured to capture reflected light from the object such as an affected region and an image pickup device not shown configured to photoelectrically convert an optical image of the object incident via the optical system and obtain an image pickup signal. The image pickup unit 23 picks up an image of the object and acquires an image pickup signal of an endoscopic image. The image pickup signal from the image pickup unit 23 is transmitted to the video processor 40 via a signal line 24 and connectors 27 and 42.

Note that the insertion portion 21 can be of a flexible type used to observe digestive organs or of a rigid type used for surgeries. The image pickup unit 23 can be provided with an image pickup device in the operation portion (grasping portion) 25 and configured to transmit an optical image from the distal end of the insertion portion to the image pickup device via an image fiber. As the image pickup unit 23, a camera head attached to an eyepiece portion of an optical endoscope (fiber scope or optical viewing tube for surgery) inserted into a body cavity may be used.

The video processor 40 includes a control unit 41, which is a controller configured to control each unit. The control unit 41 may be constructed of a processor such as a CPU not shown and configured to operate according to a program stored in a storage unit 52 and control each unit. A video processing circuit 43 receives an image pickup signal from the endoscope 20. The video processing circuit 43 applies predetermined analog signal processing such as amplification processing to the inputted image pickup signal under the control of the control unit 41 and outputs the image pickup signal to an A/D conversion circuit 44. The A/D conversion circuit 44 converts the output of the video processing circuit 43 to a digital signal and then outputs the digital signal to a white balance (WB) circuit 45. The WB circuit 45 performs white balance adjustment processing on the inputted analog image pickup signal under the control of the control unit 41 and then outputs the analog image pickup signal to an image processing circuit 46. The image processing circuit 46 applies predetermined image signal processing to the output of the WB circuit 45 under the control of the control unit 41, converts the output of the WB circuit 45 to a video signal, which can be displayed on an observation monitor 60 and then outputs the video signal to a video signal switching circuit 47.

An encoding circuit 51 captures the digital video signal outputted from the image processing circuit 46, encodes the digital video signal in a predetermined recording format and generates a video or a still image to be saved in a recording unit 65 and a recording device 80. A display controller 49 generates various screens (e.g., a setting screen, an information display screen) to be displayed on the observation monitor 60. For example, the encoding circuit 51 can convert an inputted image to a video signal in an MPEG2 format or MPEG-4AVC/H.264 format and JPEG. The encoding circuit 51 generates a still image for recording an endoscopic image and an external image.

A video signal switching circuit 47 selects either a video signal outputted from the image processing circuit 46 or a screen outputted from the display controller 49 as display contents of the observation monitor 60 according to an instruction from the control unit 41 and thereby switches an output signal. A D/A conversion circuit 48 converts the digital signal inputted from the video signal switching circuit 47 to an analog signal and outputs the analog signal to the observation monitor 60. Moreover, the D/A conversion circuit 48 can also output the analog signal to a printer 70 or a tablet 71 according to an instruction from the control unit 41.

The control unit 41 causes the encoding circuit 51 to output the image encoded by the encoding circuit 51 (encoded video signal) to a recording unit 65 and the recording unit 65 records the outputted video signal. The video processor 40 is provided with a connector 54, which is a video output terminal. An input terminal of the recording device 80 is connected to the connector 54. The control unit 41 can also give the encoded image to the recording device 80 via the connector 54 and cause the recording device 80 to record the encoded image.

The video processor 40 also can give a still image of an endoscopic image to the recording unit 65 and the recording device 80. Various recording media such as an IC memory are used as the recording unit 65. As the recording device 80, a large capacity recording medium such as a hard disk or a DVD or various storages of a file server on a network are used.

The endoscope 20 is provided with operation switches 25a configured to perform operations related to displaying or recording of an endoscopic image. A first function and a second function are assigned to the operation switches 25a. According to a time period during which a surgeon presses each operation switch 25a, any one of the functions is selected and executed. An operation signal is supplied to the control unit 41 of the video processor 40 via a signal line 26 and the connectors 27 and 42. The control unit 41 as a function setting unit includes a time detection unit 41a as a measuring unit and can detect a time period (that is, a time period during which each operation switch 25a is pressed) during which an operation signal is continuously inputted.

Note that the operation switches 25a of the endoscope 20 are preferably arranged at places where the surgeon can relatively easily operate the operation switches 25a during surgery. Although a case where the operation switches 25a are provided at the operation portion 25 of the endoscope 20 has been illustrated, the components such as buttons or various scope switches or a foot switch 67 provided in the endoscope not shown may be used as the operation switches as long as the surgeon can easily operate the components during surgery.

In the present embodiment, not only the operation switches 25a of the endoscope 20 but also a keyboard 66 is provided to control recording of endoscopic images. The surgeon performs instruction operation for processing on the video processor 40 and input operation of patient information and the like using the keyboard 66 as an input unit.

Note that the video processor 40 is provided with an operation panel 55. The operation panel 55 is a touch panel that can set the video processor 40 based on the user's operation in the same way as the keyboard 66. Settings of the video processor 40 may be made not only by the operation panel 55 or the keyboard 66 but also using an infrared remote controller or a touch panel or the like.

Figure 3:
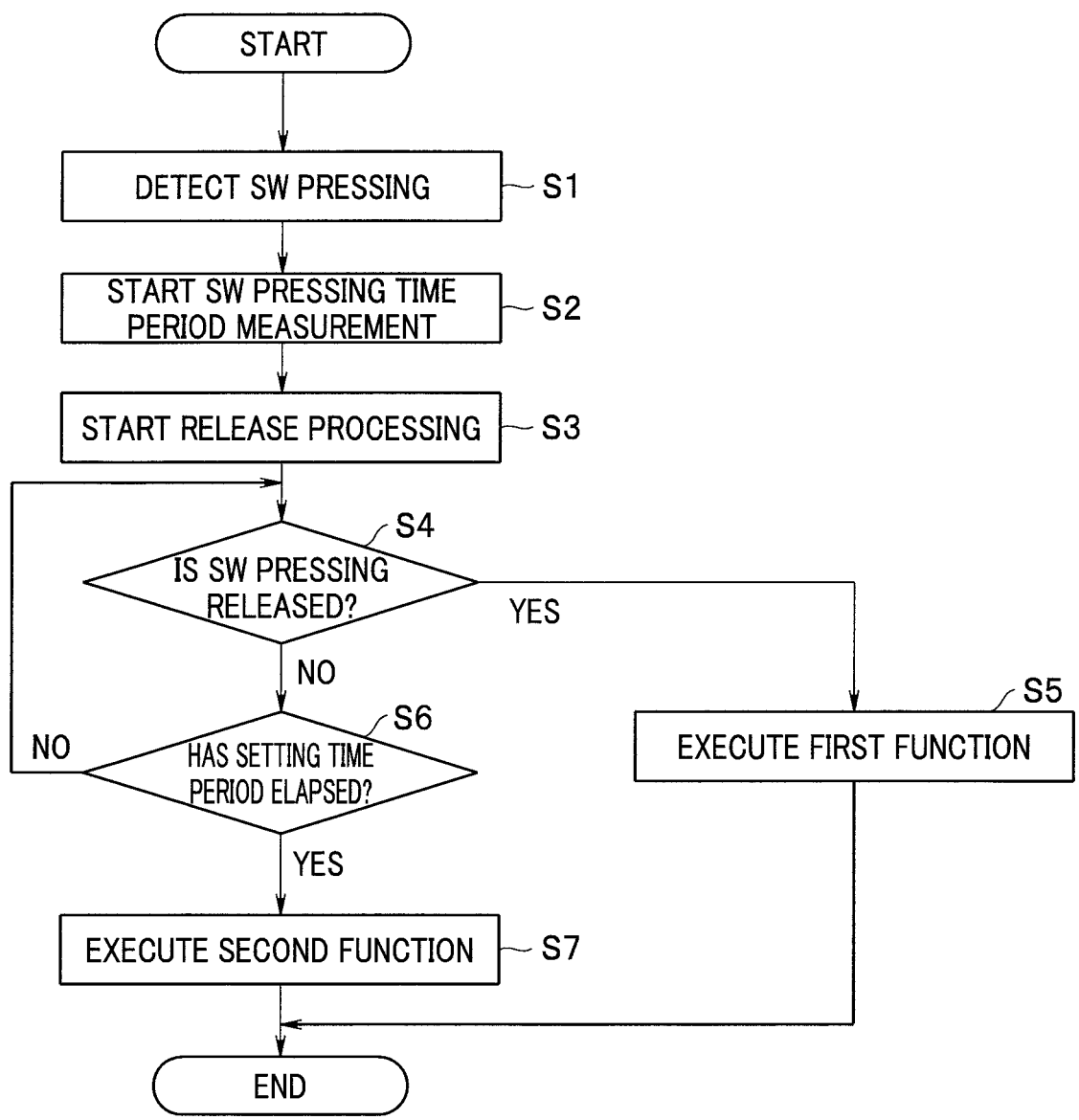
FIG. 3 is a flowchart describing a series of steps of processing an endoscopic image according to a first embodiment.
Figure 4:
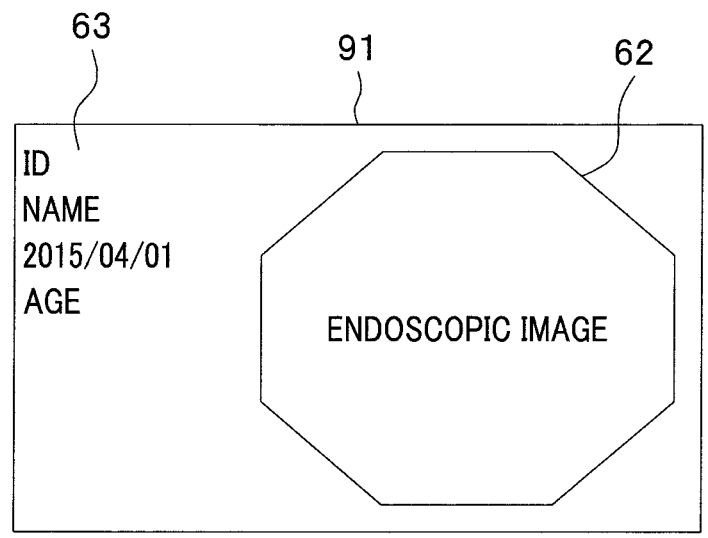
FIG. 4 is a diagram illustrating an example of screen display when a first function is executed.
Figure 5:
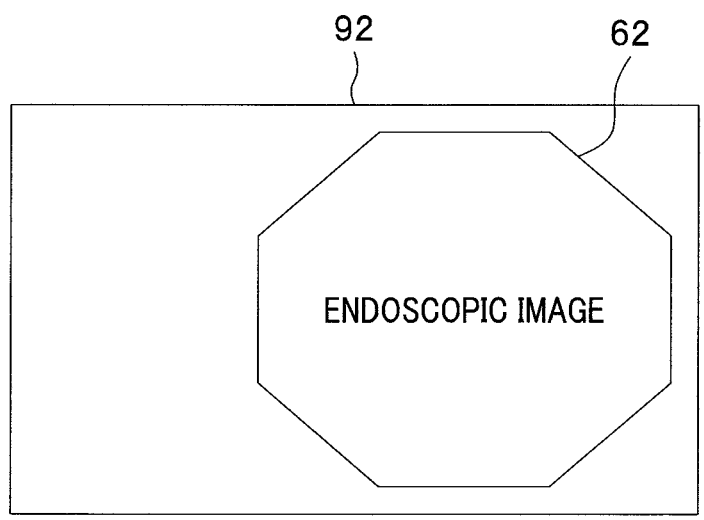
FIG. 5 is a diagram illustrating an example of screen display when a second function is executed.

Next, a control method for the endoscope system according to the embodiment will be described with reference to FIG. 3 to FIG. 5. FIG. 3 is a flowchart describing a series of steps of processing an endoscopic image of the endoscope system according to the first embodiment. FIG. 4 is a diagram illustrating an example of a screen display when a first function is executed and FIG. 5 is a diagram describing an example of screen display when a second function is executed.

Now, it is assumed that the endoscope 20 is connected to the video processor 40 as illustrated in FIG. 2 and observation of an object by the endoscope 20 is started. An image pickup signal from the image pickup unit 23 of the endoscope 20 is supplied to the video processing circuit 43 of the video processor 40 via the connectors 27 and 42. The inputted image pickup signal is subjected to predetermined analog signal processing such as amplification processing at the video processing circuit 43, converted to a digital signal by the A/D conversion circuit 44 and then supplied to the WB circuit 45. With white balance adjusted by the WB circuit 45, the image pickup signal is given to the image processing circuit 46 and subjected to predetermined image signal processing. The image processing circuit 46 outputs an endoscopic image that can be displayed on the observation monitor 60. The endoscopic image is supplied to the observation monitor 60 via the video signal switching circuit 47 and the D/A conversion circuit 48 and displayed. Note that pressing the operation switch 25a causes a still image of the endoscopic image to be saved.

In such a condition, if, for example, the surgeon presses the operation switch 25a of the endoscope 20, the control unit 41 of the video processor 40 detects an operation signal inputted from the operation switch 25a via the signal line 26 and the connectors 27 and 42 (S1).

At the same time as detecting the operation signal, the time detection unit 41a of the control unit 41 starts measuring a pressing time period of the operation switch 25a (S2). Furthermore, at the same time as detecting the operation signal, release processing is started to acquire a still image of the endoscopic image (S3).

Next, the control unit 41 monitors whether the pressing of the operation switch 25a is released (S4). More specifically, while the operation signal is continuously inputted, the control unit 41 determines that the pressing of the operation switch 25a is not released (S4, NO), and when the operation signal input ceases, the control unit 41 determines that the pressing of the operation switch 25a is released (S4, YES).

When it is determined that the pressing of the operation switch 25a is not released (S4, NO), the control unit 41 compares a first time period set and registered in advance with the storage unit 52 or the like with a pressing time period of the operation switch 25a being measured by the time detection unit 41a (S6). When the pressing time period does not exceed the first time period (S6, NO), the process returns to S4 and the control unit 41 continues monitoring whether the pressing of the operation switch 25a is released. If it is determined that the pressing of the operation switch 25a is released (S4, YES) before the first time period elapses, a predetermined first function is executed.

The first function is a function to add and record patient information, information on inspection date and time, observation parameters or the like (hereinafter described as "inspection information") to a still image of the endoscopic image. When the first function is executed, an image illustrated in FIG. 4 is recorded in a predetermined recording medium (the recording unit 65, the recording device 80 or the like).

An endoscopic image 62 picked up by the image pickup unit 23 is displayed on an image 91 in FIG. 4. Inspection information 63 is displayed outside the display region of the endoscopic image 62.

On the other hand, when the pressing time period has passed the first time period (S6, YES), that is, when the operation switch 25a is continuously pressed longer than the first time period, a predetermined second function is executed. When the second function is executed, an image as illustrated in FIG. 5 is recorded in a predetermined recording medium (the recording unit 65, the recording device 80 or the like).

Only the endoscopic image 62 picked up by the image pickup unit 23 is displayed on an image 92 in FIG. 5. Unlike the image 91 in FIG. 4, the inspection information 63 is not displayed.

Thus, in the present embodiment, a time period after the operation switch 25a is pressed until the switch pressing is released (a pressing time period) is measured, the first function is executed when the pressing time period is within a predetermined first time period set in advance (a single press) or a second function is executed when the pressing time period has passed the predetermined first time period (a long press). Therefore, since the function is switched according to the pressing time period, it is possible to switch a plurality of functions using a single operation switch without compromising operability. Furthermore, since release processing is started at timing at which the operation switch 25a is pressed, it is possible to acquire an image at desired timing of the surgeon.

Note that the time period corresponding to timing of switching functions to be executed from the first function to the second function (the first time period) is not limited to a fixed time period, but the user may set an appropriate time period. For example, the user may select a desired first time period from among predetermined alternatives for time periods (0.5 s, 1 s, 2 s, 3 s) to thereby set timing of switching functions to be executed.

The first function causes an endoscopic image with inspection information added to be saved, whereas the second function causes only an endoscopic image to be saved. In order to distinguish by which function each image is saved, two folders: a first folder and a second folder may be registered in advance with a recording medium where each image is saved (the recording unit 65, the recording device 80 or the like) so that the image acquired by the first function may be saved in the first folder and the image acquired by the second function may be saved in the second folder. The images may be saved with characters identifying by which function the image is acquired added to each image file name.

Second Embodiment

Figure 6:
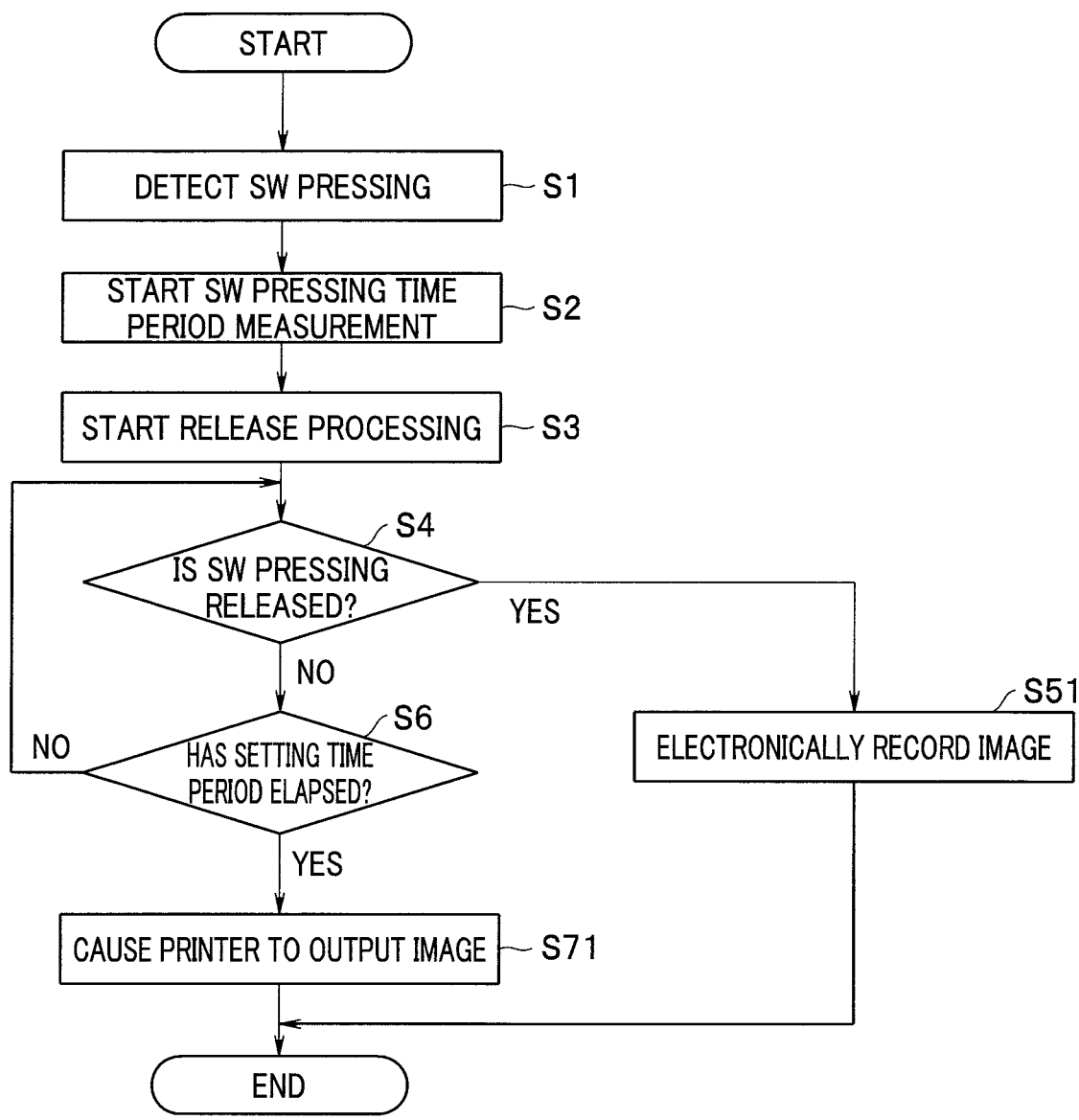
FIG. 6 is a flowchart describing a series of steps of processing an endoscopic image according to a second embodiment.

FIG. 6 is a flowchart describing a series of steps of processing an endoscope image of an endoscope system according to a second embodiment. In FIG. 6, steps identical to the steps in FIG. 3 are assigned identical reference numerals and description is omitted. A hardware configuration in the present embodiment is similar to the hardware configuration in FIG. 2.

The flowchart in FIG. 6 is different from the flowchart in FIG. 3 in that the flowchart in FIG. 6 includes S51 instead of S5 and includes S71 instead of S7. In S51, as the first function, an endoscopic image acquired at timing at which the operation switch 25a is pressed is saved in a predetermined recording medium (the recording unit 65, the recording device 80 or the like) as an electronic file (electronic data). In S71, as the second function, the endoscopic image acquired at the same timing is outputted to the printer 70 and printed on a medium such as a sheet.

Note that in S71, the endoscopic image is outputted to the printer 70 and the endoscopic image may be saved in a predetermined recording medium as an electronic file in the same way as the first function in S31.

In this way, the function assigned to the operation switch 25a may be designated as the destination to which the acquired image is outputted. In the present embodiment, it is also possible to obtain effects similar to the effects in the first embodiment.

Third Embodiment

Figure 7:
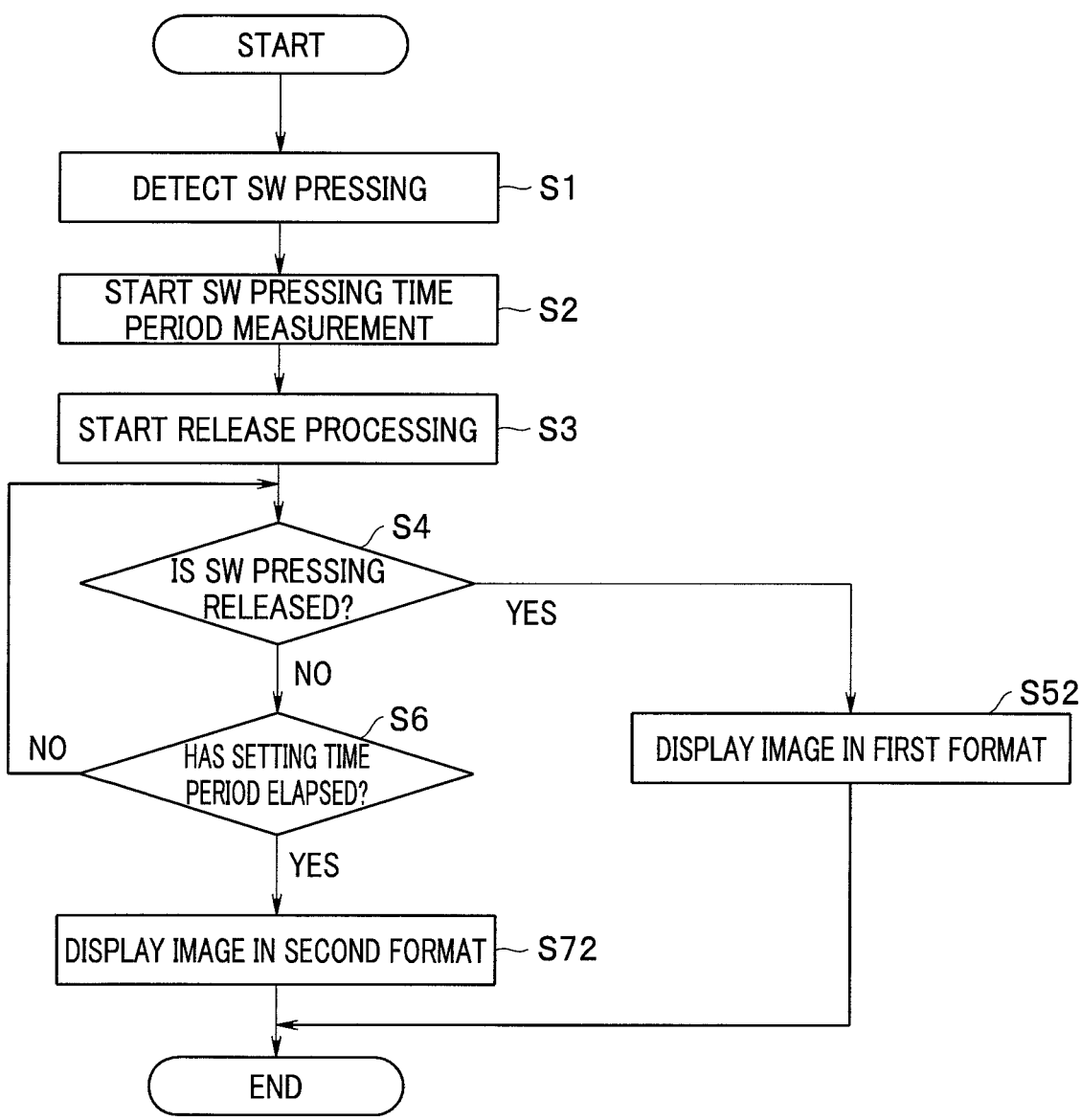
FIG. 7 is a flowchart describing a series of steps of processing an endoscopic image according to a third embodiment.

FIG. 7 is a flowchart describing a series of steps of processing an endoscope image of an endoscope system according to a third embodiment. In FIG. 6, steps identical to the steps in FIG. 3 are assigned identical reference numerals and description is omitted. A hardware configuration in the present embodiment is similar to the hardware configuration in FIG. 2.

The flowchart in FIG. 7 is different from the flowchart in FIG. 3 in that the flowchart in FIG. 7 includes S52 instead of S5 and includes S72 instead of S7. In S32, as the first function, an endoscopic image acquired at timing at which the operation switch 25a is pressed with inspection information added is displayed on the observation monitor 60. In other words, the image 91 as illustrated in FIG. 4 is displayed on the observation monitor 60. In S72, as the second function, only an endoscopic image acquired at the same timing is displayed on the observation monitor 60 (inspection information is not added). In other words, the image 92 as illustrated in FIG. 5 is displayed on the observation monitor 60.

In this way, the function assigned to the operation switch 25a may be designated as a display format when the acquired image is displayed on the observation monitor 60 or the like. In the present embodiment, it is also possible to obtain effects similar to the effects in the first embodiment.

Note that the acquired image not only may be displayed on the observation monitor 60 but also may be saved in a predetermined recording medium using an electronic file (electronic data). In this case, an image with inspection information added may be saved in S52, and an image without inspection information added may be saved in S72. In both S52 and S72, images with inspection information added may be saved in an electronic file.

At the same timing as starting the release processing in S3, the first function in S52 may be executed, the image 91 as illustrated in FIG. 4 may be displayed on the observation monitor 60, and when the pressing time period has passed the predetermined first time period (S6, YES), the functions may be switched to display the image 92 as illustrated in FIG. 5.

Next, modifications of the aforementioned three embodiments will be described.

(Modification 1)

Figure 8:
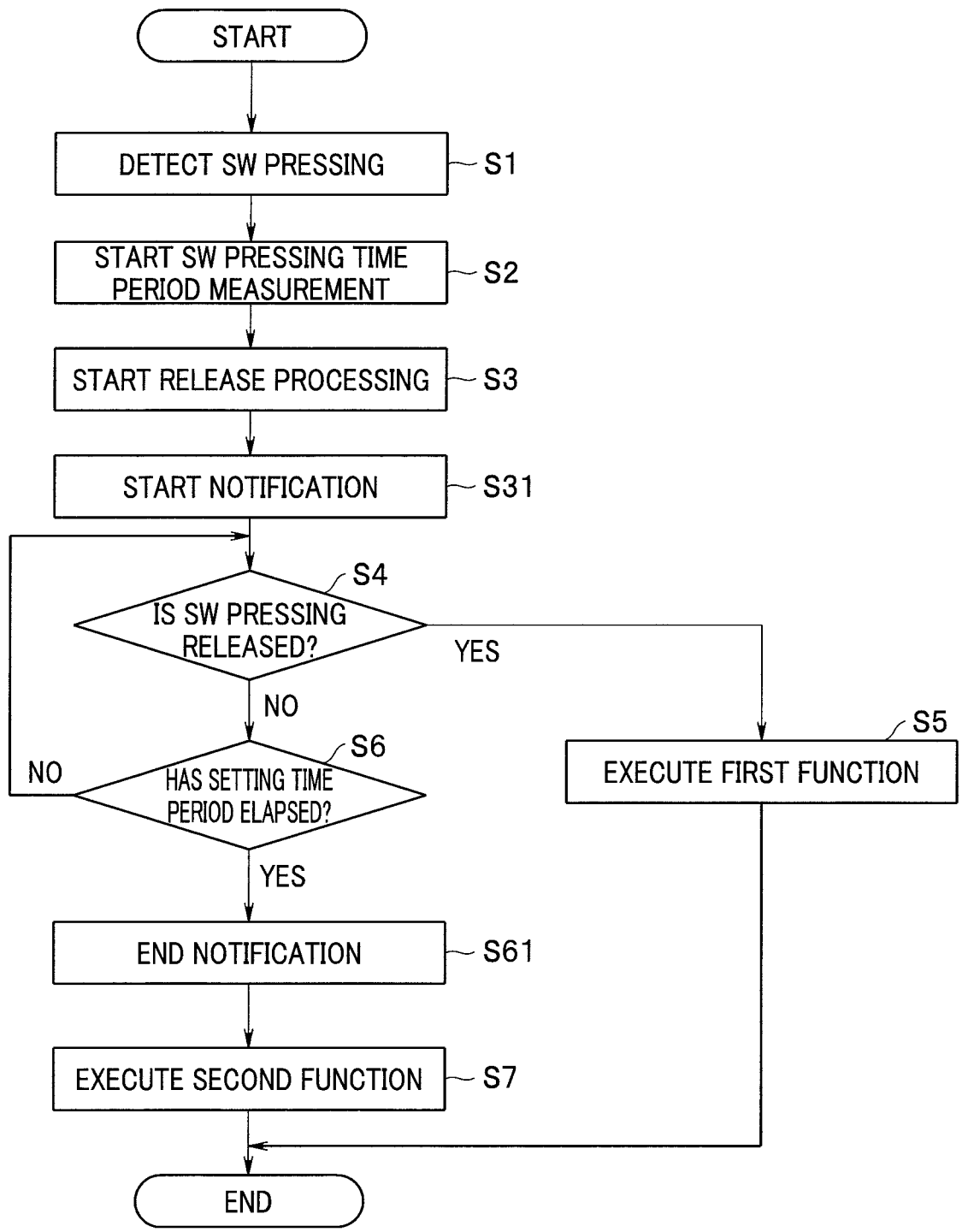
FIG. 8 is a flowchart describing a series of steps of processing an endoscopic image according to modification 1.

FIG. 8 is a flowchart describing a series of steps of processing an endoscopic image of an endoscope system according to a modification. In FIG. 8, steps identical to the steps in FIG. 3 are assigned identical reference numerals and description is omitted. A hardware configuration in the present modification is similar to the hardware configuration in FIG. 2.

The flowchart in FIG. 8 is different from the flowchart in FIG. 3 in that S31 is executed after S3 and S61 is executed after S6. In S3, at timing of starting release processing, the process proceeds to S31 without delay to start notification by a buzzer tone or the like. In S6, when a pressing time period has passed the predetermined first time period (S6, YES), the process proceeds to S61 without delay to end the notification started in S31 by stopping the buzzer tone or the like.

Thus, notification with a buzzer tone or the like is performed during the first time period during which the first function can be executed, and when the pressing time period has passed the first time period and the endoscope system is ready to execute the second function, notification is ended, and the surgeon can thereby easily recognize how long to keep the operation switch 25a pressed to further improve operability.

Note that when a photographing function is normally executed, an endoscopic image needs to be kept frozen in order to capture an inspection image and complete saving, and so a certain time period is provided after photographing as a still time (a release time). If the first time period is set to the same time as the release time, the surgeon can easily recognize not only timing of switching between functions but also the release time.

(Modification 2)

Figure 9:
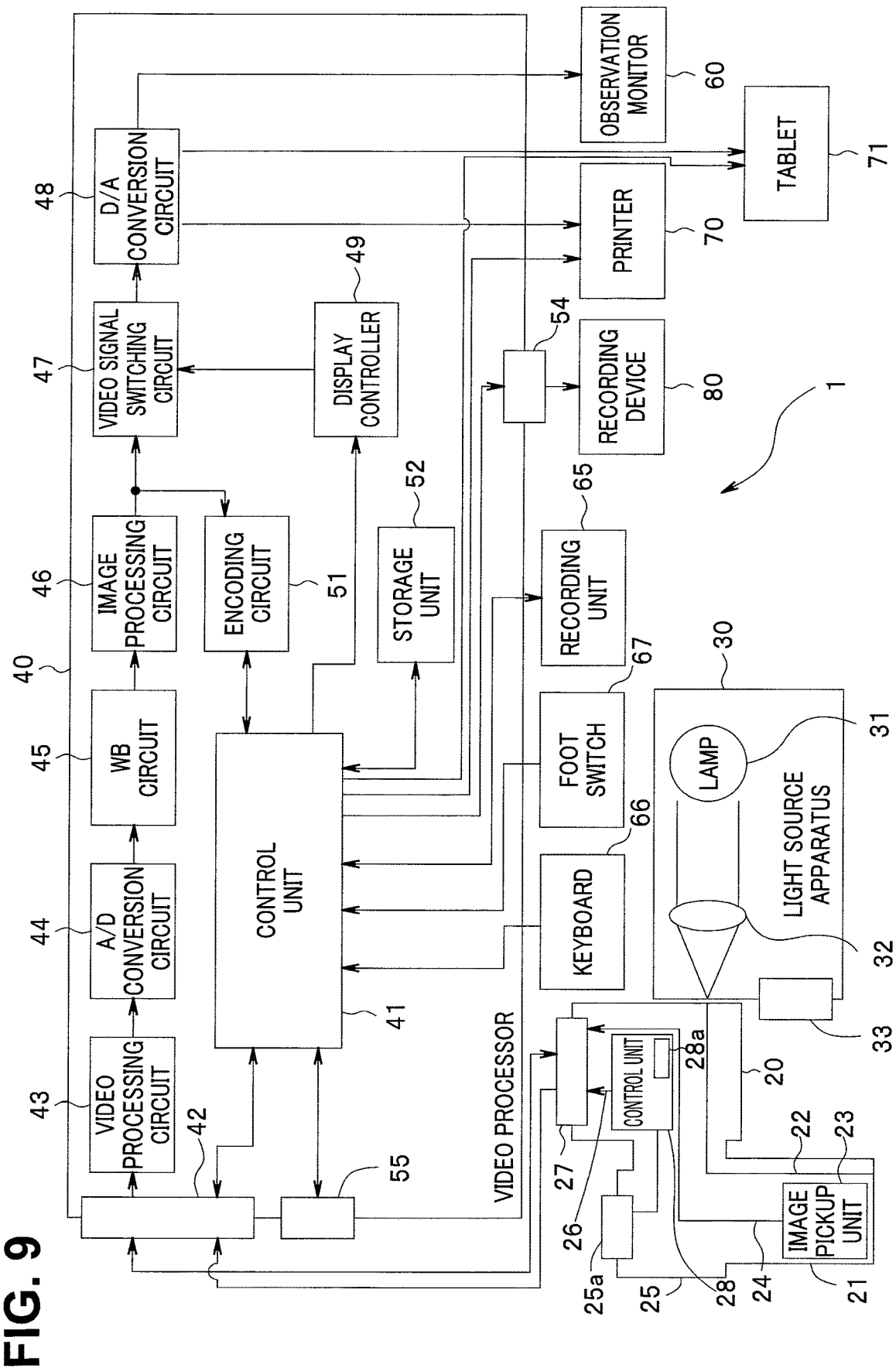
FIG. 9 is a block diagram illustrating a detailed configuration of an endoscope system according to modification 2.

FIG. 9 is a block diagram illustrating a detailed configuration of an endoscope system according to modification 2. In FIG. 9, components identical to the components in FIG. 2 are assigned identical reference numerals and description is omitted.

The endoscope system of the present modification is different from the endoscope system in FIG. 2 in that the endoscope 20 is provided with a control unit (a controller) 28 including a time detection unit 28a. In other words, in the present modification, the control unit 28 of the endoscope 20 performs the function to detect a pressing time period of the operation switch 25a and select which of the first function or the second function assigned to the operation switch 25a to perform, which has been performed by the control unit 41 of the video processor 40.

Thus, according to the present modification, effects similar to the effects in the aforementioned respective embodiments can be obtained and the processor needs only to execute processing according to a control signal inputted from the endoscope 20, and conventional processors can be used, providing higher versatility.

Fourth Embodiment

The endoscope 20 may be provided with a plurality of operation switches 25a and each operation switch 25a may be assigned two functions. Not only the operation switches 25a but also the foot switch 67 or the keyboard 66 may be used to input an operation instruction to the video processor 40. In such a case, it takes time for the user to remember what function is assigned to which input device during an observation, which may constitute obstruction to the observation.

Figure 10:
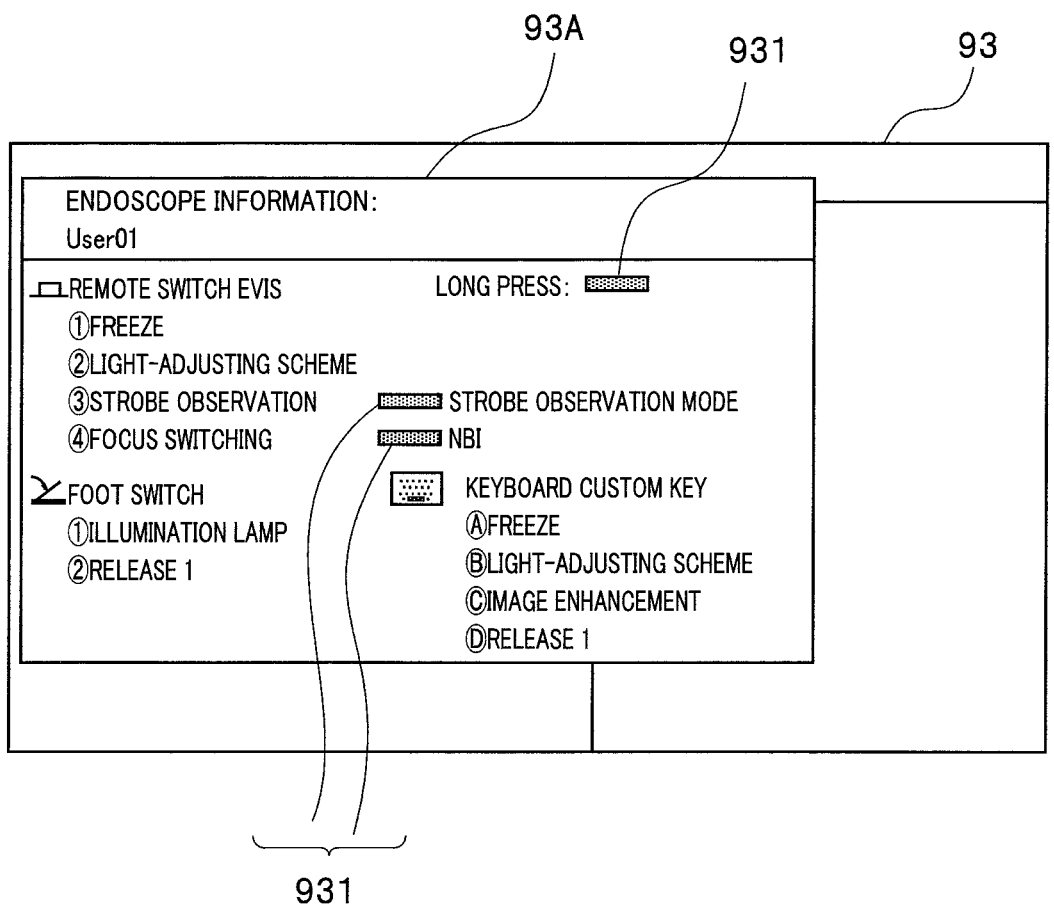
FIG. 10 is a diagram illustrating an example of a switch information display screen according to a fourth embodiment.

Therefore, in the present embodiment, a screen to display function assignment information is provided to thereby provide efficient observation work. FIG. 10 is a diagram illustrating an example of a switch information display screen according to a fourth embodiment. Note that a hardware configuration in the present embodiment is similar to the configuration in FIG. 2. In other words, the control unit 41 includes a display control unit (not shown) configured to display a switch information display screen.

A switch information display screen 93A is superimposed, for example, on a display screen 93 of the display apparatus of the observation monitor 60 and displayed. Devices for inputting operation instructions to the video processor 40 and functions assigned to the respective devices are listed on the switch information display screen 93A. In an example in FIG. 10, four operation switches 25a (labeled "remote switch EVIS" in FIG. 10), two foot switches 67 and the keyboard 66 are used as input devices. In the keyboard 66, functions are individually assigned to predetermined four keys A to D.

For example, the third and fourth operation switches 25a of the remote switch EVIS are set so as to input different functions in cases of the single press and the long press to the processor 40. The other input devices are assigned one function to each. In this case, as illustrated in FIG. 10, the switch information display screen 93A displays one corresponding function of the respective devices of the first and second operation switches 25a, the first and second foot switches 67 and the first to fourth keys A to D for operation input of the keyboard 66. For example, a freeze function is assigned to the first operation switch 25a. For example, an "illumination lamp" control function is assigned to the first foot switch 67. Furthermore, for example, an "image enhancement" function is assigned to the third key C of the keyboard 66.

By contrast, the remote switches EVIS (3, 4) assigned two functions are displayed in such a way that the function for single press and the function for long press are easily identifiable. For example, as illustrated in FIG. 10, the function for single press and the function for long press are displayed side by side, and an icon 931 to identify the long-press function is added at the top of the display of the function for long press. For example, the third operation switch 25a (3) is assigned a "strobe observation" function for single press and assigned a "strobe observation mode" switching function for long press. Furthermore, for example, the fourth operation switch 25a (4) is assigned a "focus switching" function for single press and assigned an "NBI" observation mode switching function for long press.

In this way, in the present embodiment, names of a plurality of input devices (switches) for function setting and switching, and functions assigned to the respective devices are listed and displayed on the display apparatus. Furthermore, when one device is assigned two functions (function pair), a condition for executing each function (single press/long press) is also displayed on the screen. Therefore, the user can easily identify an input device configured to execute a desired function and thereby improve efficiency of observation work.

Note that the switch information display screen 93A may also be superimposed on other screens such as the display screen of the operation panel 55 instead of the display screen 93 of the observation monitor 60 to be displayed. Furthermore, instead of superimposing the screen on other screens, the switch information display screen 93A may be singly displayed by switching the screens.

Fifth Embodiment

Figure 11:
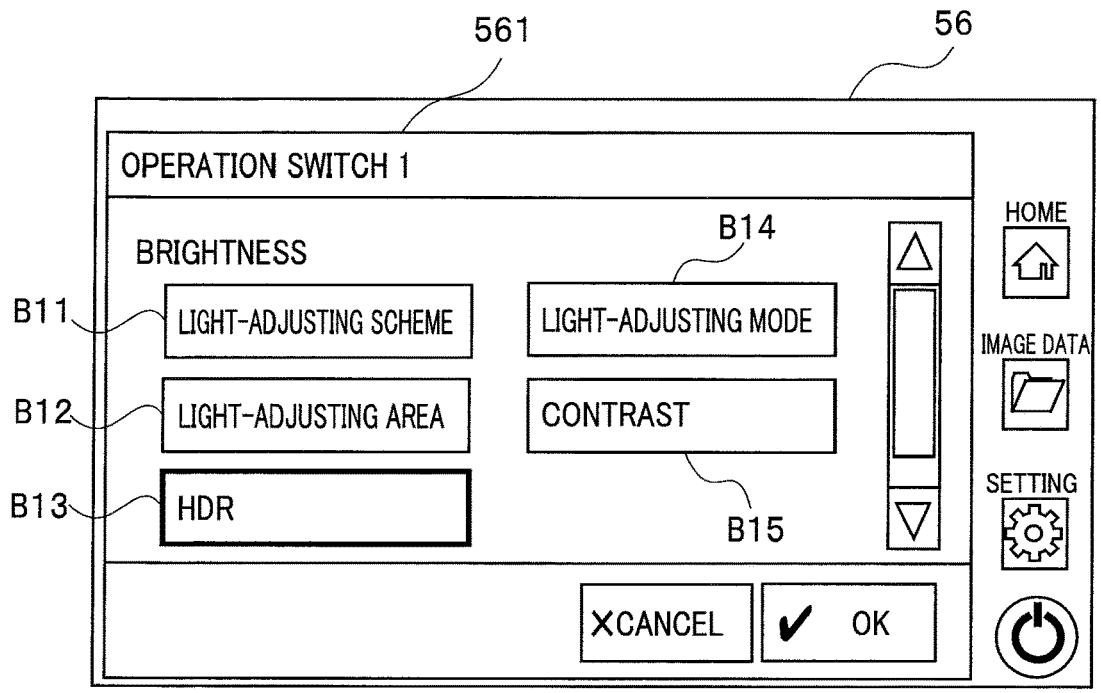
FIG. 11 is a diagram illustrating an example of an operation switch function setting screen according to a fifth embodiment.
Figure 12:
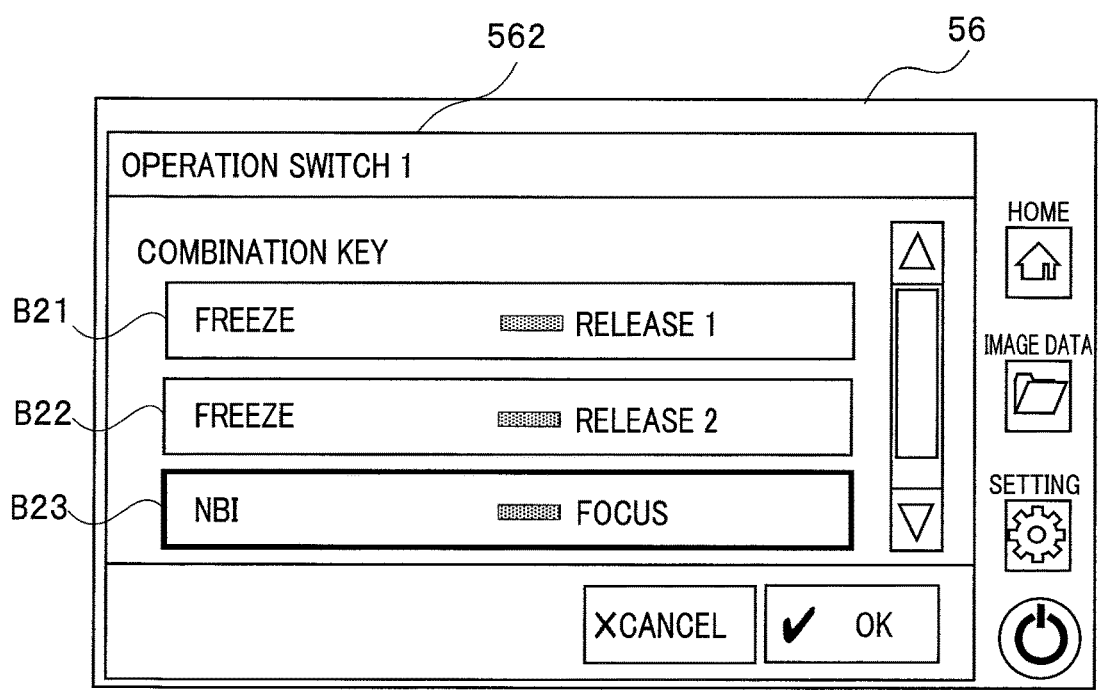
FIG. 12 is a diagram illustrating an example of an operation switch function setting screen according to the fifth embodiment.

An endoscope system according to the present embodiment includes a setting function capable of switching between the first function executed in a single-press state of the operation switch 25a and the second function executed in a long-press state in accordance with the use or purpose of the endoscope or user preferences or the like. FIG. 11 and FIG. 12 are each a diagram illustrating an example of an operation switch setting screen. FIG. 11 illustrates a setting screen when only one function is set for the operation switch 25a and FIG. 12 illustrates a setting screen when two functions are set for the operation switch 25a.

An operation switch setting screen 56 is displayed, for example, on the operation panel 55 of the video processor

40. First, a case where only one function is set for the operation switch 25*a* will be described. As illustrated in FIG. 11, the operation switch setting screen 56 is provided with a function selection region 561. A plurality of radio buttons B11 to B15 are arranged in the function selection region 561. The respective radio buttons B11 to B15 are assigned alternatives for functions settable for the operation switches 25*a*. The radio buttons B11 to B15 have, for example, horizontal rectangle shape and the assigned functions are displayed on the respective buttons. For example, the radio button B11 is assigned a function to switch light-adjusting scheme ("light-adjusting scheme" in FIG. 11). When the user presses the radio button B11, a light-adjusting scheme switching function is set for the operation switch 25*a*.

Next, two functions (function pair) are settable for the operation switch 25*a* and a case where the two functions are set will be described. As illustrated in FIG. 12, the operation switch setting screen 56 is provided with a function selection region 562. The function selection region 562 is provided with a plurality of radio buttons B21 to B23. Each radio button B21 to B23 is assigned alternatives for two functions (first function and second function) settable for the operation switch 25*a*. Each radio button B21 to B23 has, for example, a horizontal rectangle shape and the assigned functions are displayed on the respective buttons. For example, the radio button B21 is assigned a freeze function as a first function and a release 1 function as a second function. When the user presses the radio button B21, the freeze function is set for the operation switch 25*a* in the case of single press for a first time period or shorter and the release 1 function is set in the case of long press longer than the first time period.

In the present embodiment, when two functions are set for the operation switch 25*a*, the two functions are selected as a combination (pair) instead of selecting two settable functions individually. If the user has mistakenly operated a single press for a long press (e.g., if the user has performed a long press when the user should have performed a single press, or has performed a single press when the user should have performed a long press), recording may be stopped during surgery depending on the combination of functions.

Therefore, functions to be set for "single press" and "long press" are set and registered as function pairs in advance. In the function selection region 562 of the operation switch setting screen 56, the radio buttons B21 to B23 set by the control unit 41 and assigned the function pairs respectively are displayed on the operation panel 55. An example of possible function pairs is shown below.

(a) Single Press: Freeze Function, Long Press: Release Function

The "freeze function" is a function of the control unit (display control unit) 41 to freeze an endoscopic image being displayed on the display apparatus such as the observation monitor 60. The "release function" is a function of the control unit 41 to save an endoscopic image being displayed on the display apparatus as a still image. Still images are recorded in a predetermined recording medium (the recording unit 65, the recording device 80 or the like). Note that the release function is set depending on a recording destination of a still image, like release 1 function, release 2 function, . . . . During use, the function pair is a combination of functions highly related to each other.

(b) Single Press: NBI Mode, Long Press: Optical Expansion Mode

Both are setting functions in observation mode. The "NBI mode" is a mode to display the structure of a surface layer of a mucous membrane in an easily observable manner with narrow-band light in optical digital observation. The "optical expansion mode" is a function to realize more delicate work or diagnosis by optically moving an expansion display lens group, thereby changing an angle of view or focal length to enable detailed observation of blood vessels, nerves and tissues by near focus observation. By assigning functions used in different scenes to the single press and the long press respectively, it is possible to prevent erroneous operation by the user.

(c) Single Press: Optical Expansion Mode, Long Press: NBI Mode

As for the function pair used in (b), functions assigned to the single press and the long press are reversed. Depending on the user's preference, (b) and (c) can be used interchangeably.

(d) Single Press: One Touch AF, Long Press: Continuous AF

Both are focusing functions in the image pickup unit 23. The "one touch AF" is a function to achieve focus within a detection range at timing scanned by the user's operation. The "continuous AF" is a function to achieve focus whereby after the user's operation, the video processor 40 automatically achieves focus within the detection range. Assigning focusing-related functions to the same operation switch 25*a* improves operability by the user.

(e) Single Press: NBI Mode, Long Press: Orientation

"Orientation" is a function to rotate an endoscopic image 180 degrees to display. By combining functions differing in both frequency and purpose of use, assigning a more frequently used NBI mode to the single press and assigning less frequently used orientation to the long press makes it possible to efficiently use one operation switch 25*a* while preventing erroneous operation by the user.

In this way, the present embodiment provides a setting screen to set functions to be assigned to the operation switch 25*a*. Radio buttons on which functions settable for the operation switch 25*a* (the first function only or the function pairs of the first function and the second function) are displayed are arranged on the setting screen and the functions are set for the operation switch 25*a* when the user presses a desired radio button. When two functions are assigned, the functions are set using a screen similar to a case where one function is assigned and using a similar procedure, and so it is possible to assign functions to the operation switch 25*a* without compromising the user's operability.

In other words, the control unit 41 sets a plurality of function pairs, each of which is composed of a combination of any one of a plurality of first functions and any one of a plurality of second functions and assigns one function pair selected from the plurality of function pairs to the operation switch. The settable functions are registered with the video processor 40 in advance, and it is thereby possible to set function pairs that can be safely observed for the operation switch 25*a* and improve safety and efficiency in observation or inspection using the endoscope system.

Although several embodiments of the present invention have been described, these embodiments have been presented as examples and are not intended to limit the scope of the present invention. The novel embodiments can be implemented in various other forms, and various omissions, replacements or changes can be made within the scope not departing from the gist of the present invention. Such embodiments and modifications are included in the scope and gist of the invention and included in the invention described in claims and the range of equivalency.

What is claimed is:

1. An endoscope system comprising:
an endoscope comprising a switch, the switch is assigned a first function and a second function; and
a controller comprising hardware, the controller being configured to:
start a measurement of a switch pressing period from when the switch is pressed,
acquire and record an endoscopic image at a timing when the switch is pressed,
determine whether a pressing of the switch is released,
in response to the determining that the pressing of the switch is not released, determine whether the switch pressing period is smaller or larger than a predetermined first period,
execute the first function in response to the determining that the switch pressing period is smaller than the predetermined first period, and in response to the determining that the pressing of the switch is released wherein the executing of the first function comprises executing a first instruction to record the endoscopic image,
execute the second function in response to the determining that the switch pressing period is larger than the predetermined first period, and in response to the determining that the pressing of the switch is not released, and
display the acquired endoscopic image as a still image during the switch pressing period prior to the executing of the first function and the executing of the second function.

2. The endoscope system according to claim 1, wherein the executing of the first function comprises executing the first instruction to record the endoscopic image acquired by an endoscope with inspection information.

3. The endoscope system according to claim 2, wherein the executing of the second function comprises executing an instruction to record the endoscopic image without the inspection information.

4. The endoscope system according to claim 1, wherein the executing of the second function comprises executing an instruction to print the endoscopic image on a predetermined medium.

5. The endoscope system according to claim 1, wherein the executing of the second function comprises executing an instruction to display the endoscopic image without inspection information.

6. The endoscope system according to claim 1, wherein the endoscope comprising an operation portion including the switch.

7. The endoscope system according to claim 1, wherein the switch is a foot switch.

8. The endoscope system according to claim 1, wherein the controller is configured to cause a notification from when the switch is pressed to when the controller determines that the switch pressing period is larger than the first period.

9. The endoscope system according to claim 1, wherein the executing of the second function comprises displaying the endoscopic image acquired at the timing when the switch is pressed as a still image.

10. The endoscope system according to claim 1, further comprising:
a plurality of switches including the switch; and
a display configured to display a plurality of functions assigned to the respective plurality of switches.

11. The endoscope system according to claim 1, wherein the controller is further configured to:
receive first information of the first function selected from a plurality of functions,
receive second information of the second function selected from the plurality of functions, and
assign the selected functions to the switch based on the first and second information.

12. The endoscope system according to claim 1, wherein the controller is further configured to:
set the first function and the second function from each of a plurality of function pairs, and
assign one function pair selected from the plurality of function pairs to the switch.

13. The endoscope system according to claim 1, wherein the controller is configured to execute the second function based only on the determining that the switch pressing period is larger than the predetermined first period.

14. The endoscope system according to claim 1, wherein the executing of the second function is performed based on the endoscopic image.

15. The endoscope system according to claim 1, wherein the controller is configured to repeat the determining of whether the pressing of the switch is released and the determining of whether the switch pressing period is smaller or larger than the predetermined first period until the executing of one of the first function and the second function.

16. A control method of an endo scope system, the method comprising:
starting a measurement of a switch pressing period from when a switch is pressed;
acquiring and recording an endoscopic image at a timing when the switch is pressed,
determining whether a pressing of the switch is released,
in response to the determining that the pressing of the switch is not released, determining whether the switch pressing period is smaller or larger than a predetermined first period,
executing a first function in response to determining that the switch pressing period is smaller than the predetermined first period and in response to the determining that the pressing of the switch is released, wherein the executing of the first function comprises executing a first instruction to record the endoscopic image,
executing a second function in response to determining that the switch pressing period is larger than the predetermined first period, and in response to the determining that the pressing of the switch is not released, and
display the acquired endoscopic image as a still image during the switch pressing period prior to the executing of the first function and the executing of the second function.

17. A non-transitory computer-readable storage medium that stores a control program of an endoscope system, the control program causing a computer to:
start a measurement of a switch pressing period from when a switch is pressed;
acquire and record an endoscopic image at a timing when the switch is pressed,
determine whether a pressing of the switch is released,
in response to the determining that the pressing of the switch is not released, determine whether the switch pressing period is smaller or larger than a predetermined first period,
execute a first function in response to determining that the switch pressing period is smaller than the predetermined first period, wherein the executing of the first function comprises executing a first instruction to record the endoscopic image and in response to the determining that the pressing of the switch is released, executing a second function in response to determining that the switch pressing period is larger than the predetermined first period, and in response to the determining that the pressing of the switch is not released, and displaying the acquired endoscopic image as a still image during the switch pressing period prior to the executing of the first function and the executing of the second function.

\* \* \* \* \*